United States Patent [19]

Dimicoli et al.

[11] 4,153,688
[45] May 8, 1979

[54] TRIFLUOROMETHYLATED OLIGOPEPTIDES

[75] Inventors: Jean-Luc Dimicoli, Orsay; Camille G. Wermuth; Joseph G. Bieth, both of Strasbourg, all of France

[73] Assignee: Delalande S.A., Courbevoie, France

[21] Appl. No.: 876,500

[22] Filed: Feb. 9, 1978

[30] Foreign Application Priority Data

Feb. 18, 1977 [FR] France .................................. 77 04713

[51] Int. Cl.² ...................... A61K 37/00; C07C 103/52
[52] U.S. Cl. ............................. 424/177; 260/112.5 R
[58] Field of Search ................... 260/112.5 R; 424/177

[56] References Cited

U.S. PATENT DOCUMENTS 3,985,723  10/1976  Panetta et al. ................. 260/112.5 R

FOREIGN PATENT DOCUMENTS 938782  2/1960  United Kingdom ................... 260/112.5

*Primary Examiner*—Delbert R. Phillips
*Attorney, Agent, or Firm*—Blanchard, Flynn, Thiel, Boutell & Tanis

[57] ABSTRACT

A compound having the formula

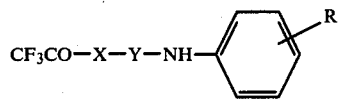

wherein
(1) —X—Y— is -L-Ala-L-Ala- and R is H, m-NO$_2$, m-CF$_3$, p-Cl, p-NO$_2$, p-CF$_3$, p-OCH$_3$, p-CH(CH$_3$)$_2$, p-CN or p-COOH,
(2) —X—Y— is -L-Lys-L-Ala- and R is H, p-CF$_3$, p-CH$_3$, p-CH(CH$_3$)$_2$,

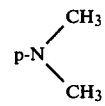

or p-COCH$_3$
(3) —X—Y— is

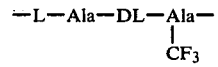

and R is H, or
(4) —X—Y— is -L-Lys-L-Lys or L-Ala-L-Lys and R is p-CF$_3$.

The compounds are reversible inhibitors of porcine pancreatic elastase and human lentocytal elastase.

12 Claims, No Drawings

TRIFLUOROMETHYLATED OLIGOPEPTIDES

The present invention concerns novel trifluoromethylated oligopeptides, the method of preparation thereof and their application in therapeutics.

More exactly, these new compounds correspond to the formula:

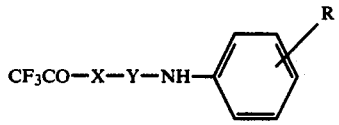 (I)

in which the couple -X-Y- represents:
either the sequence -L-Ala-L-Ala-, in which case R designates:
  a hydrogen atom;
  a nitro or trifluoromethyl group in the meta position; or
  a chlorine atom or a nitro, trifluoromethyl, methoxy, isopropyl, cyano or carboxyl group in the para position;
or the sequence -L-Lys-L-Ala-, in which case R designates:
  a hydrogen atom: or
  a trifluoromethyl, methyl, isopropyl, N, N-dimethylamino or acetyl group in the para position;
or the sequence

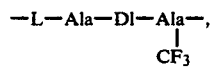

in which case R designates a hydrogen atom;
or the sequence -L-Lys-L-Lys- or L-Ala-L-Lys-, in which case R represents a trifluoromethyl group in the para position.

For the sake of simplicity we represent, in what follows, the different above-mentioned sequences respectively in the following way: -Ala-Ala-; -Lys-Ala-;

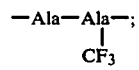

-Lys-Lys-; and -Ala- Lys-; it being understood that -Ala- and -Lys- are of L configuration and that

is of DL configuration.

The compounds of formula (I), in which the couple —X—Y— represents the sequences -Lys-Ala-, -Ala-Lys- and -Lys-Lys-, are obtained by using a process which consists in hydrogenolysing respectively the compounds of formulae:

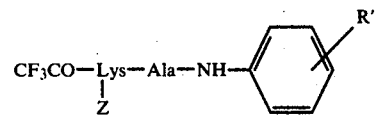 (I'),

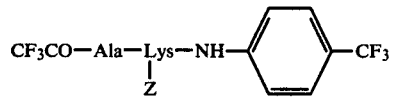 (I''), and

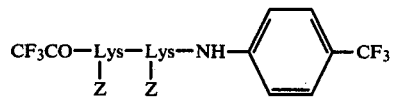 (I''')

in which Z represents the benzyloxycarbonyl group; and R represents a hydrogen atom or a trifluoromethyl, methyl, isopropyl, N, N-dimethylamino or acetyl group in the para position.

The hydrogenolysis reaction is particularly carried out in the presence of palladium on charcoal at 10% and of hydrochloric acid, in a methanol solution, the hydrochloric acid being preferably normal.

The compound of formula (I) in which the couple —X—Y— represents the sequence

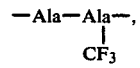

is obtained by condensing trifluoroacetic acid methyl ester with the compound of formula:

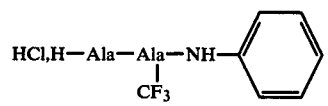 (II)

for example, according to the method described by Weygand and Geiger in Chem. Ber. 92, 2099 (1959).

The compounds of formula (I) in which the couple —X—Y— represents the sequence -Ala-Ala- and R designates a para-nitro or meta-trifluoromethyl group, are obtained by condensing trifluoroacetic acid anhydride with the compounds of formula:

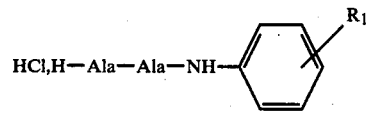 (III)

in which $R_1$ represents a para-nitro or meta-trifluoromethyl group, in the presence of a Lewis base.

Finally, the compounds of formula (I) in which the couple —X—Y— represents the sequence -Ala-Ala- and R designates a hydrogen atom or a m-nitro, p-chloro, p-trifluoromethyl, p-methoxy, p-isopropyl, p-cyano, or p-carboxyl group, are obtained by condensing the compound of formula:

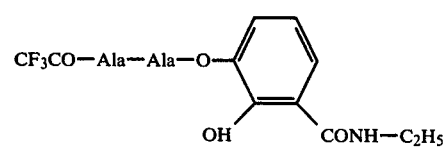 (IV)

with anilines of formula:

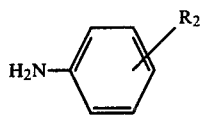

in which $R_2$ has the same meanings as those given for R just above formula (IV)

This condensation is preferably achieved in tetrahydrofuran and in the presence of tetramethylguanidine.

The compounds of formula (I'), they also being novel, are obtained:

by condensing trifluoroacetic acid methyl ester with the compounds of formula:

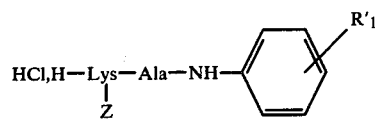

where $R'_1$ designates a hydrogen atom or a para-trifluoromethyl group, Z being a benzyloxycarbonyl group, and by condensing the compound of formula:

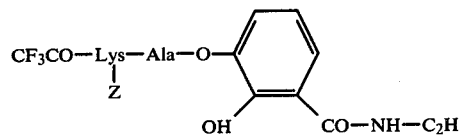

where Z has the same meaning as in formula (VI), with anilines of formula:

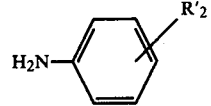

where $R'_2$ designates a p-methyl, p-isopropyl, p-N,N-dimethylamino or p-acetyl group.

These two condensation reactions may be carried out particularly following the method described previously.

The new compounds of formulae (I″) and (I‴) are respectively obtained by condensing trifluoroacetic acid methyl ester with the compound of formula:

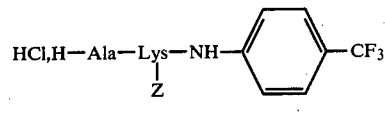

and the compound of formula:

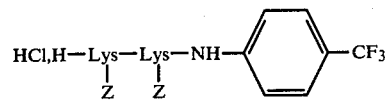

in which formulae Z is the benzyloxycarbonyl group, these condensations being carried out in accordance with the above-mentioned Weygand and Geiger method.

The novel compounds of formulae (II), (III), (VI), (IX) and (X) are obtained respectively by deprotection of the compound of formula:

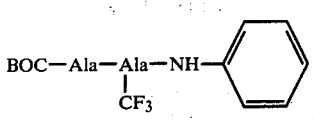

of the compounds of formula:

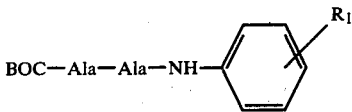

where $R_1$ has the same meaning as in formula (III), of the compound of formula:

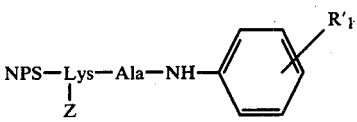

where $R'_1$ has the same meaning as in formula (VI), of the compound of formula:

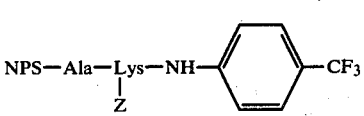

of the compound of formula

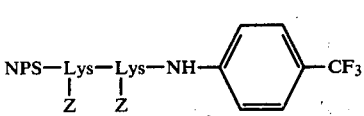

BOC designating the tertiobutoxycarbonyl group, Z the benzyloxycarbonyl group and NPS the para-nitrophenylsulfenyl group.

It should be noted that when the protection group is BOC, the deprotection is preferably carried out in an acetic acid solution and in the presence of hydrochloric acid 2 N. When the protection group is NPS, the deprotection is preferably carried out in solution in an acetone-ethyl ether mixture and in presence of hydrochloric acid 4 N.

The compounds of formulae (IV) and (VII), also new, result from the condensation of hydroxy-7 N-ethyl-isobenzoxazolinium tetrafluoroborate of formula:

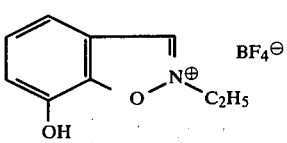

with the compounds of formulae:

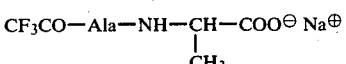

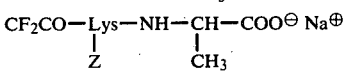

in which Z represents a benzyloxycarbonyl group, these compounds themselves resulting from the action of an aqueous solution of sodium bicarbonate on the corresponding acids of formulae:

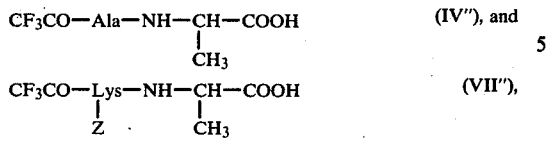

Z having the same meaning as previously.

This condensation reaction is preferably achieved in the presence of pyridine, in solution in a water-ethyl acetate mixture and by adjusting the pH of the solution to 4.5–5 with hydrochloric acid 3 N.

The compounds of formulae (IV″) and (VII″) are obtained by condensation of the dipeptides of formulae:

where Z has the same meaning as previously, with trifluoroacetic acid thioethyl ester.

The new compound of formula (II′) is obtained by condensing the compound of formula:

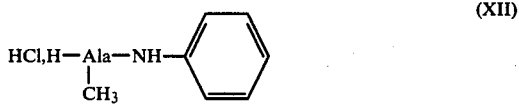

with protected amino-acid of formula:

where BOC has the same meaning as previously, following the mixed anhydrides method.

The compounds of formula (III′), partially new, are obtained by condensing the compounds of formula:

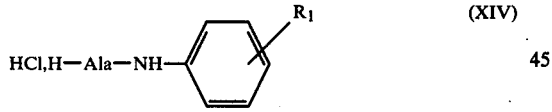

where $R_1$ has the same meaning as in formula (III), with tertiobutyloxycarbonyl-L-alanine para-nitrophenyl ester of formula:

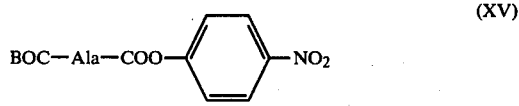

The compounds of formula (VI′), new, are obtained by condensing the compounds of formula:

where $R'_1$ has the same meaning as in formula (VI), with the dicyclohexylammonium of protected lysine of formula:

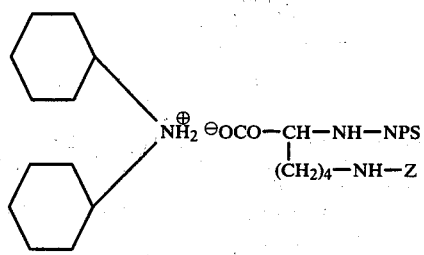

in which Z and NPS have the same meaning as previously, following the dicyclohexylcarbodiimide method.

The experimental protocols of these different condensations are in accordance with those described, for example, by:

Bodanszky, M. and Odetti, M. A. in Peptide Synthesis (1966), Intersciences Publishers (Lavoisier), and Law, H. D. The organic chemistry of Peptides - Wiley Intersciences (1970).

The new compound of formula (IX′) is obtained by condensing the compound of formula:

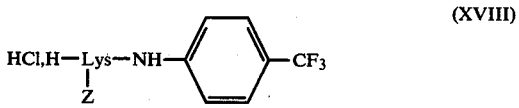

where Z has the same meaning as previously, with the compound of formula:

preferably following the mixed anhydrides method.

As for the new compound of formula (X′), it is obtained by condensing the compound of formula (XVIII) with the compound of formula (XVII), following the dicyclohexylcarbodiimide method.

The compounds of formulae (XII), (XIV), (XVI) and (XVIII), partially novel, are obtained by deprotection respectively:

of the compound of formula:

of the compound of formula:

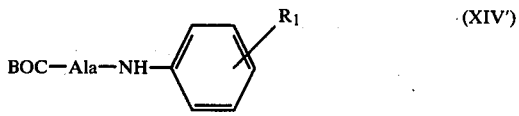

where $R_1$ has the same meaning as in formula (III), of the compounds of formula:

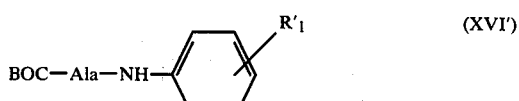

where $R'_1$ has the same meaning as in formula (VI), of the compound of formula:

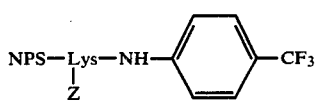
(XVIII')

Z, BOC and NPS having the same meanings as previously. The elimination of these three protection groups takes place preferably in the conditions already stated above (see preparation of compounds (I) from (I'), (I'') and (I''') when the protection group is Z, and preparation of compounds (II), (III), (VI), (IX) and (X) when the protection group is NPS or BOC).

Finally, the new compounds of formulas (XII'), (XIV'), (XVI') and (XVIII') result respectively:
from the condensation of aniline on protected amino-acid of formula:

(XX)

where Z has the same meaning as previously,
from the condensation of the anilines of formula:

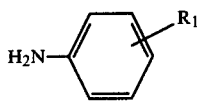
(XXI)

where $R_1$ has the same meaning as in formula (III), on protected aminoacid of formula (XIII),
from the condensation of the anilines of formula:

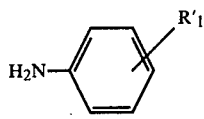
(XXII)

where $R'_1$ has the same meaning as in formula (VI), on protected aminoacid of formula (XIII),
from the condensation of aniline of formula:

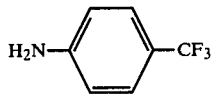
(XXIII)

on protected amino-acid of formula:

(XXIV)

where Z and NPS have the same meanings as previously.

The first three condensations are preferably carried out following the the mixed anhydrides method, the last one being preferably carried out following the dicyclohexylcarbodiimide method.

The preparations below are described by way of examples to illustrate the invention.

EXAMPLE 1

Trifluoroacetyl-L-lysyl-L-alanyl-p-trifluoromethylanilide hydrochloride.

Code number: 12

A solution of 2 g of N-α-trifluoroacetyl N-ε-carbobenzoxy-L-lysyl-L-alanyl-p-trifluoromethylanilide (code number: 21, prepared according to example 2 below) in 50 ml of methanol was hydrogenolysed at room pressure and temperature, in the presence of palladium in charcoal at 10% and 1.2 equivalent of hydrochloric acid 1 N. Then the obtained solution is filtered and the solvent evaporated.

Yield: 35%
Melting point: 163°–167° C.
$[\alpha]_{546}^{25} = -62°4$ (1,CH$_3$OH)
Empirical formula: $C_{18}H_{23}ClF_6N_4O_3$
Molecular weight: 492.85

| Elementary analysis : | C | H | N |
|---|---|---|---|
| calculated (%) | 43.87 | 4.7 | 11.37 |
| obtained (%) | 41.65 | 4.95 | 10.05 |

By using the same process, but from corresponding reagents, compounds of code numbers 11, 13, 14, 15, 16, 18 and 19, listed in table A below, were obtained.

EXAMPLE 2

N-α-trifluoroacetyl N-ε-carbobenzoxy-L-lysyl-L-alanyl-p-trifluoromethylanilide

Code number: 21

To a solution of 3.5 g of N-ε-carbobenzoxy-L-lysyl-L-alanyl-p-trifluoromethylanilide hydrochloride (code number: 44, prepared in accordance with example 5 below) in 150 ml of chloroform, was added 1.8 ml of triethylamine, then 9 ml of trifluoroacetic acid methyl ester. It was stirred for 30 hours, then evaporated dry, taken up again in methanol, water was added, the product was filtered, dried and purified by chromatography on a silica column with elution by means of a chloroform-methanol mixture (80/20). Thus, 2.3 g of the desired product were isolated.

Yield: 62%
Melting point: 202°–203° C.
$[\alpha]_{546}^{25} = -46°5$ (1, CH$_3$ OH)

| Elementary analysis : | C | H | N |
|---|---|---|---|
| calculated (%) | 52.88 | 4.78 | 9.49 |
| obtained (%) | 53.07 | 4.89 | 9.33 |

By using the same process, but from the corresponding reagents, compound of code number 17, given in table A below, as well as compounds of code numbers 20, 26 and 27, given in table B below, were obtained.

EXAMPLE 3

N-trifluoroacetyl-L-alanyl-L-alanyl-p-nitroanilide

Code number: 3

To a suspension of 5 g of L-alanyl-L-alanyl-p-nitroanilide hydrochloride (code number 46, prepared in accordance with example 6 below) in 70 ml of anhydrous methylene chloride were added 15 ml of anhydrous triethylamine. It was evaporated dry, taken up again with a second portion of methylene chloride an again evaporated dry. To the residue were added 100 ml of anhydrous methylene chloride and 2.2 ml of anhydrous triethylamine then, with stirring and drop by drop, 3.3 g of trifluoro-acetic acid anhydride in 20 ml of dry methylene chloride. After stirring for 15 hours at room temperature, it was evaporated dry. The residue was taken up again with water, allowed to crystallize, filtered and the precipitate washed with water. Thus were obtained 1.1 g of white crystals after two recrystallizations in a water-acetic acid mixture.
Yield: 37%
Melting point: 218° C.
Molecular weight: 376
Empirical formula: $C_{14}H_{15}F_3N_4O_5$

| Elementary analysis : | C | H | N |
|---|---|---|---|
| calculated (%) | 44.52 | 4.12 | 14.98 |
| obtained (%) | 44.68 | 4.02 | 14.89 |

By using the same process, but from the corresponding reagents, compound of code number 6, given in table A below, was obtained.

EXAMPLE 4

N-trifluoroacetyl-L-alanyl-L-alanylanilide

Code number: 1

To a suspension of 0.001 mole of N-trifluoroacetyl-L-alanyl-L-alanyl o-hydroxy, m-ethylamidophenyl ester (code number 54, prepared in accordance to example 10 below) in 1 ml of tetrahydrofuran, were added 0.0011 mole of aniline and 0.0011 mole of tetramethylguanidine. The reaction, the evolution of which is observed by infra-red spectroscopy, was continued until the ester band at 1750 cm$^{-1}$ disappeared. Then the solvent was evaporated, water added and recrystallization carried out.
Yield: 46%
Melting point: 259°–260° C.
$[\alpha]_{546}^{25} = -134°6$ (1, $CH_3OH$)
Molecular weight: 331.3
Empirical formula: $C_{14}H_{16}F_3N_3O_3$

| Elementary analysis : | C | H | N |
|---|---|---|---|
| calculated (%) | 50.75 | 4.87 | 12.68 |
| obtained (%) | 50.41 | 4.60 | 12.72 |

By using the same process, but from the corresponding reagents, the compounds of code numbers 2, 4, 5, 7, 8, 9 and 10, shown in table A below and compounds of code numbers 22, 23, 24 and 25, shown in table B below, were obtained.

EXAMPLE 5

N-ε-carbobenzoxy-L-lysyl-L-alanyl-p-trifluoromethylanilide hydrochloride.

Code number: 44

To a solution of 7 g of N-ε-p-nitrophenylsulfenyl N-ε-carbobenzoxy-L-lysyl-L-alanyl-p-trifluoromethylanilide (code number 28, prepared in example 7) in 100 ml of ethyl acetate and 10 ml of acetone, were added 5.4 ml of a solution of hydrochloric acid 4 N in ethyl ether. It was stirred for 20 minutes, then petroleum ether was added, and the oil obtained was decanted and crystallized in an ether-petroleum ether mixture. It was filtered and dried.
Yield: 92%
Melting point: 110°–113° C.
$[\alpha]_{546}^{25} = -4°1$ (1, $CH_3OH$)

By using the same process, but from the corresponding reagents, the following compounds were obtained:

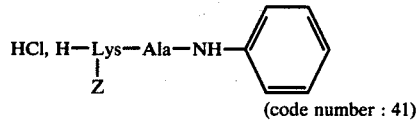
(code number : 41)

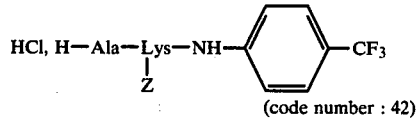
(code number : 42)

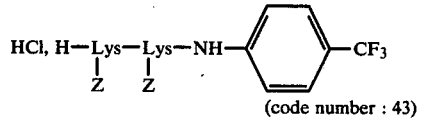
(code number : 43)

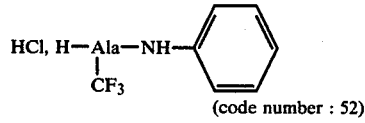
(code number : 52)

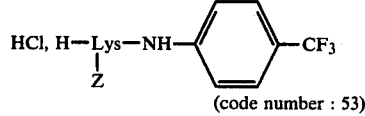
(code number : 53)

It should be noted that all these compounds are used in the crude state in the synthesis where they play a role.

EXAMPLE 6

L-alanyl-L-alanyl m-trifluoromethylanilide hydrochloride

Code number: 45

The reaction mixture formed by solution of 1.61 g of N-tertiobutyloxycarbonyl-L-alanyl-L-alanyl m-trifluoromethylanilide (code number 34, prepared in example 9) in 8 ml of acetic acid containing 292 mg of gaseous hydrochloric acid, was left at rest for 30 minutes, then the solvent was evaporated and the residue crystallized in ether.

By using the same process, but from the corresponding reagents, the following compounds were obtained:

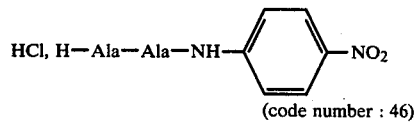
(code number : 46)

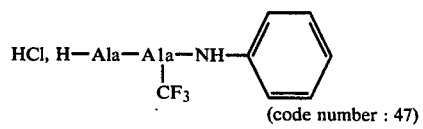
(code number : 47)

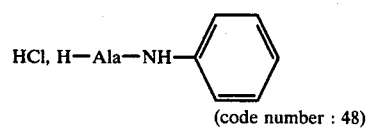
(code number : 48)

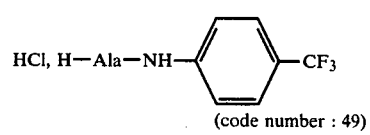
(code number : 49)

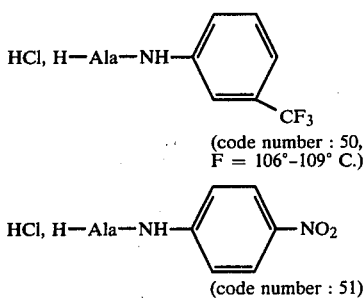

(code number : 50,
F = 106°-109° C.)

HCl, H—Ala—NH—⟨benzene ring⟩—NO₂

(code number : 51)

These different compounds are used in the crude state in the synthesis in which they play a role.

EXAMPLE 7

N-α-p-nitrophenylsulfenyl N-ε-carbobenzoxy-L-lysyl-L-alanyl p-trifluoromethylanilide Code number: 28

To a suspension of 6.3 g of dicyclohexylammonium N-α-p-nitrophenylsulfenyl N-ε-carbobenzoxy-L-lysinate in 100 ml of chloroform were added 2.72 g of L-alanyl-p-trifluoromethylanilide hydrochloride (code number 49, prepared in accordance with the process of example 6). Stirring was carried out until a solution was obtained, it was cooled to −20° C. and 2.2 g of dicyclohexylcarbodiimide were added. It was left lying cold for 2 hours, then for one night at room temperature, the solvent was evaporated, the residue was dissolved in tetrahydrofuran and the obtained solution was filtered; the filtrate was evaporated and the residue taken up again in chloroform. The solution was concentrated, diluted with isopropyl ether, filtered and the obtained product was recrystallized in isopropylic alcohol.

Yield: 73%
Melting point: 117°-118° C.
$[\alpha]_{546}^{25} = -94°6$ (1, CH₃OH)
Empirical formula: $C_{29}H_{30}SF_3N_4O_5$
Molecular weight: 603.6

| Elementary analysis : | C | H | N |
|---|---|---|---|
| calculated (%) | 55.63 | 4.98 | 10.81 |
| obtained (%) | 55.73 | 4.89 | 10.50 |

Using the same process, but from the corresponding reagents, compounds of code numbers 29 and 30, shown in table C below, were obtained.

EXAMPLE 8

N-p-nitrophenylsulfenyl-L-alanyl N-ε-carbobenzoxy-L-lysyl p-trifluoromethylanilide Code number: 32

To a solution of 0.01 mole of N-para-nitrophenylsulfenyl-L-alanine in 100 ml of tetrahydrofuran, cooled to −15° C., were added 0.01 mole of ethyl chloroformate and 0.01 mole of N-methylmorpholine. It was stirred for 15 minutes, then a mixture of 0.01 mole of N-ε-carbobenzoxy-L-lysyl-para-trifluoromethylanilide hydrochloride (code number 53, prepared according to example 5) and 0.01 mole of N-methylmorpholine was added. It was stirred for 1 hour at −15° C. and for 2 hours at room temperature, and filtered, the solvent was evaporated and the residue dissolved in chloroform. It was washed with a 5% aqueous solution of potassium hydrogenosulfate, with water, with a 5% aqueous solution of sodium bicarbonate and with water. It was dried, the solution was concentrated, diluted with petroleum ether and the crystals obtained were filtered.

Yield: 66%
Melting point: 227°-229° C.
$[\alpha]_{546}^{25} = -53°4$ (0.5; CH₃OH)
Empirical formula: $C_{29}H_{30}F_3SN_4O_5$
Molecular weight: 603.6

| Elementary analysis : | C | H | N |
|---|---|---|---|
| calculated (%) | 55.63 | 4.98 | 10.81 |
| obtained (%) | 55.68 | 4.99 | 10.78 |

By using the same process, but from the corresponding reagents, compound of code number 31, shown in table C below, was obtained.

EXAMPLE 9

Tertiobutyloxycarbonyl-L-alanyl-L-alanyl m-trifluoromethylanilide

Code number: 34

To a solution of 4.7 g of L-alanyl-metatrifluoromethylanilide hydrochloride (code number 50, prepared according to example 6) in 40 ml of methylene chloride, were added 4.85 ml of triethylamine; the solvent was evaporated, the residue taken up again in 30 ml of methylene chloride, a few drops of triethylamine and 5.4 g of tertiobutyloxycarbonyl-L-alanyl para-nitrophenyl ester were added. They were left in contact for 15 minutes at room temperature, the solvent was evaporated, the residue taken up again in a 50/50 mixture of hexane and isopropyl ester. The obtained solution was filtered, and the precipitate obtained was recrystallized in a mixture of ether and isopropyl alcohol.

Yield: 56%
Melting point: 175° C.
Empirical formula: $C_{18}H_{24}F_3N_3O_4$
Molecular weight: 403.4

By using the same process, but from the corresponding reagents, compound of code number 33, shown in table C below, was obtained.

EXAMPLE 10

N-trifluoroacetyl-L-alanyl-L-alanyl-2-hydroxy 3-ethylamidophenyl ester

Code number: 54

The pH of a solution of 1.8 g of trifluoroacetyl-L-alanyl-L-alanine (prepared in example 13) in 14.1 ml of ethyl acetate and 0.8 ml of pyridine was adjusted to 4.5-5 with aqueous hydrochloric acid 3 N and 2 g of hydroxy-7 N-ethylisobenzoxazolinium tetrafluoroborate were added over 20 minutes. The obtained solution was diluted with ethyl acetate, the organic phase was washed with an aqueous solution of hydrochloric acid 3 N, with a 5% solution of sodium bicarbonate and with water. The solvent was evaporated, the residue taken up again in ether, filtered and recrystallized in ethyl acetate.

Yield: 72%
Melting point: 195°-197° C.
$[\alpha]_{546}^{25} = -84°5$ (1, DMSO)

| Elementary analysis : | C | H | N |
|---|---|---|---|
| claculated (%) | 48.69 | 4.80 | 10.02 |

-continued

| Elementary analysis : | C | H | N |
|---|---|---|---|
| obtained (%) | 48.54 | 4.61 | 10.98 |

By using the same process, but from the corresponding reagents, the following compound:

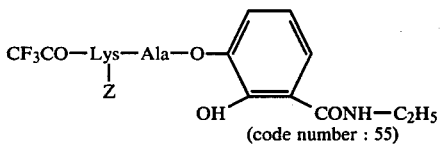

(code number : 55)

was obtained.

This compound is used in the crude state for the synthesis of the compounds of code numbers 22, 23, 24 and 25.

EXAMPLE 11

Tertiobutyloxycarbonyl-L-alanyl p-trifluoromethylanilide

Code number: 35

The synthesis of this compound is carried out in accordance with the process described in example 8, from para-trifluoromethylaniline and tertiobutyloxycarbonyl-L-alanine.

Yield: 77%
Melting point: 158°–159° C.
$[\alpha]_{546}^{25} = -50°$ (1, $CH_3OH$)
Empirical formula $C_{15}H_{19}F_3N_2O_3$
Molecular weight: 332.3

| Elementary analysis : | C | H | N |
|---|---|---|---|
| calculated (%) | 54.21 | 5.76 | 8.48 |
| obtained (%) | 54.42 | 5.62 | 7.94 |

With the same process, but from the corresponding reagents the compounds of code number 36 and 39, listed in table D below, were obtained.

EXAMPLE 12

N-α-p-nitrophenylsulfenyl N-ε-benzyloxycarbonyl-L-lysyl p-trifluoromethylanilide Code number: 40

The synthesis of this compound is carried out in accordance with the process of example 7, from p-trifluoromethylaniline and N-α-p-nitrophenylsulfenyl N-ε-benzyloxycarbonyl-L-lysine.

Yield: 35%
Melting point: 136°–138° C.
$[\alpha]_{546}^{25} = 0°3$ (1, $CH_3OH$)
Empirical formula: $C_{26}H_{25}SF_3N_4O_5$
Molecular weight: 562.6

| Elementary analysis : | C | H | N |
|---|---|---|---|
| calculated (%) | 56.24 | 4.72 | 9.72 |
| obtained (%) | 56.20 | 4.75 | 9.38 |

With the same process, but starting from the corresponding reagents, the compounds of code numbers 37 and 38, shown in table D below, were obtained.

EXAMPLE 13

Trifluoroacetyl-L-alanyl-L-alanine

Compound of formula (IV''')

To a solution of 1.5 g of Ala-Ala in 9.25 ml of aqueous soda 1 N, was added 1.9 ml of ethyl trifluorothioacetate and the obtained mixture was stirred for 20 hours at room temperature. Then it was acidified to pH 3 with hydrochloric acid 1 N, extracted with ethyl acetate, the solvent was evaporated and the obtained product crystallized in petroleum ether.

Yield: 78%
Melting point: 160°–163° C.
$[\alpha]_{546}^{25} = -81°$ (1, $CH_3OH$)

With the same process, but from the corresponding reagents, the compound of formula:

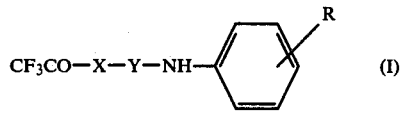

was obtained.

Tables A, B, C and D below show respectively:
the compounds of formula (I);
the compounds of formulae (I'), (I'') and (I''');
the compounds of formulae (II'), (III'), (VI'), (IX') and (X'); and
the compounds of formulae (XII'), (XIV'), (XVI') and (XVIII').

TABLE A

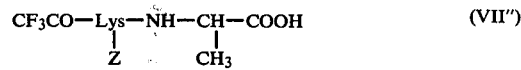

| Code No. | R | —X—Y— | Emperical formula | Molecular Wt. | Melting Point (°C.) | Yield (%) | $[\alpha]_{546}^{25}$ | Calculated (%) C | H | N | Obtained (%) C | H | N |
|---|---|---|---|---|---|---|---|---|---|---|---|---|---|
| 1 | H | —Ala—Ala— | $C_{14}H_{16}F_3N_3O_3$ | 331.3 | 250–260 | 46 | −134°6 (1, $CH_3OH$) | 50.75 | 4.87 | 12.68 | 50.41 | 4.60 | 12.72 |
| 2 | 4Cl | " | $C_{14}H_{15}ClF_3N_3O_3$ | 365.7 | 253–255 | 44 | −131°5 (1, $CH_3OH$) | 45.97 | 4.14 | 11.5 | 45.05 | 4.07 | 11.14 |
| 3 | 4$NO_2$ | " | $C_{14}H_{15}F_3N_4O_5$ | 376 | 218 | 37 | | 44.52 | 4.12 | 14.98 | 44.68 | 4.02 | 14.89 |
| 4 | 3$NO_2$ | " | $C_{14}H_{15}F_3N_4O_5$ | 376.3 | 209–210 | 33 | −131°7 (1, $CH_3OH$) | 44.69 | 4.02 | 14.89 | 44.57 | 3.74 | 14.59 |
| 5 | 4$CF_3$ | " | $C_{15}H_{15}F_6N_3O_3$ | 399.3 | 253–254 | 30 | −114°5 (1, $CH_3OH$) | 45.12 | 3.79 | 10.52 | 44.72 | 3.67 | 9.81 |
| 6 | 3$CF_3$ | " | $C_{15}H_{15}F_6N_3O_3$ | 399.3 | 194 | 63 | | 45.12 | 3.79 | 10.52 | 44.98 | 3.66 | 10.52 |

TABLE A-continued $$CF_3CO-X-Y-NH-\underset{}{\underset{}{\bigcirc}}-R \qquad (I)$$

| Code No. | R | —X—Y— | Emperical formula | Molecular Wt. | Melting Point (°C.) | Yield (%) | $[\alpha]_{546}^{25}$ | Calculated (%) C | H | N | Obtained (%) C | H | N |
|---|---|---|---|---|---|---|---|---|---|---|---|---|---|
| 7 | 4CH$_3$O | " | C$_{15}$H$_{18}$F$_3$N$_3$O$_4$ | 361.3 | 271–272 | 56 | −46°9 (1, DMF) | 49.86 | 5.02 | 11.63 | 49.47 | 4.98 | 12.26 |
| 8 | 4—⟨ | " | C$_{17}$H$_{22}$F$_3$N$_3$O$_3$ | 373.4 | 249–251 | 57 | −124° (1, CH$_3$OH) | 54.68 | 5.93 | 11.25 | 54.79 | 5.90 | 10.86 |
| 9 | 4CN | " | C$_{15}$H$_{15}$F$_3$N$_4$O$_3$ | 356.3 | 204–205 | 34 | −127°8 (1, CH$_3$OH) | 50.56 | 4.24 | 15.72 | 48.41 | 3.82 | 15.35 |
| 10 | 4COOH | " | C$_{15}$H$_{16}$F$_3$N$_3$O$_5$ | 375.3 | 268–272 (decomp) | 40 | −139°8 (1, CH$_3$OH) | 48 | 4.3 | 11.2 | 48.43 | 4.17 | 12.24 |
| 11 | H | —Lys—Ala— | C$_{17}$H$_{24}$ClF$_3$N$_4$O$_3$ | 424.85 | 150–153 | 30 | −68°7 (1, CH$_3$OH) | 48.06 | 5.69 | 13.19 | 45.83 | 5.45 | 12.79 |
| 12 | 4CF$_3$ | " | C$_{18}$H$_{23}$ClF$_6$N$_4$O$_3$ | 492.85 | 163–167 | 35 | −62°4 (1, CH$_3$OH) | 43.87 | 4.7 | 11.37 | 4.165 | 4.95 | 10.05 |
| 13 | 4CH$_3$ | " | C$_{18}$H$_{26}$ClF$_3$N$_4$O$_3$ | 438.9 | 134–146 | 91 | −69°3 (1, CH$_3$OH) | | | | | | |
| 14 | 4—⟨ | " | C$_{20}$H$_{30}$ClF$_3$N$_4$O$_3$ | 466.9 | 135–145 | 92 | −66°8 (1, CH$_3$OH) | | | | | | |
| 15 | 4-N(CH$_3$)CH$_3$ | " | C$_{19}$H$_{29}$ClF$_3$N$_5$O$_3$ | 504.4 | 135–149 | 93 | −60°9 (1, CH$_3$OH) | | | | | | |
| 16 | 4-COCH$_3$ | " | C$_{17}$H$_{26}$ClF$_3$N$_4$O$_4$ | 466.9 | 153–160 | 90 | −66°8 (1, CH$_3$OH) | | | | | | |
| 17 | H | —Ala—Ala— (CF$_3$) | C$_{14}$H$_{13}$F$_6$N$_3$O$_3$ | 385.27 | 246 | 55 | | 43.65 | 3.40 | 10.91 | 43.66 | 3.12 | 11.24 |
| 18 | 4CF$_3$ | —Lys—Lys— | C$_{21}$H$_{31}$Cl$_2$F$_6$N$_5$O$_3$ | 386.41 | Hygroscopic | 70 | −33°4 (1, MeOH) | 43.01 | 5.33 | 11.94 | 40.92 | 5.25 | 11.29 |
| 19 | 4CF$_3$ | —Ala—Lys— | C$_{18}$H$_{23}$ClF$_6$N$_4$O$_3$ | 492.85 | 190–195 | 65 | −65°8 (0,5-MeOH) | 43.87 | 4.70 | 11.37 | 41.50 | 4.46 | 50.59 |

TABLE B $$CF_3CO-Lys(Z)-Ala-NH-\underset{}{\underset{}{\bigcirc}}-R' \qquad (I')$$

$$CF_3CO-AF-Lys(Z)-NH-\underset{}{\underset{}{\bigcirc}}-CF_3 \qquad (I'')$$

$$CF_3CO-Lys(Z)-Lys(Z)-NH-\underset{}{\underset{}{\bigcirc}}-CF_3 \qquad (I''')$$

| Code Number | R' | Formula | Empirical formula | Molecular Weight | Melting Point (°C.) | Yield (%) | $[\alpha]_{546}^{25}$ | Calculated (%) C | H | N | Obtained (%) C | H | N |
|---|---|---|---|---|---|---|---|---|---|---|---|---|---|
| 20 | H | I' | C$_{25}$H$_{28}$F$_3$N$_4$O$_5$ | 521.5 | 202 | 65 | −52°6 (1, CH$_3$OH) | | | | | | |
| 21 | 4CF$_3$ | " | C$_{26}$H$_{28}$F$_6$N$_4$O$_5$ | 590.5 | 202–203 | 62 | −46°5 (1, CH$_3$OH) | 52.88 | 4.78 | 9.49 | 53.07 | 4.89 | 9.33 |
| 22 | 4CH$_3$ | " | C$_{26}$H$_{31}$F$_3$N$_4$O$_5$ | 536.5 | 200–205 | 78 | −51°8 (1, CH$_3$OH) | | | | | | |
| 23 | 4—⟨ | " | C$_{28}$H$_{35}$F$_3$N$_4$O$_5$ | 564.6 | 185–188 | 47 | −53°2 (1, CH$_3$OH) | | | | | | |
| 24 | 4-N(CH$_3$)CH$_3$ | " | C$_{27}$H$_{34}$F$_3$N$_5$O$_5$ | 565.6 | 208–211 | 60 | −62°7 (1, CH$_3$OH) | | | | | | |
| 25 | 4COCH$_3$ | " | C$_{27}$H$_{31}$F$_3$N$_4$O$_6$ 564.5 | | 171–175 | 43 | −54°0 (1, CH$_3$OH) | | | | | | |
| 26 | — | I'' | C$_{26}$H$_{28}$F$_6$N$_4$O$_5$ | 590.5 | 190–195 | 60 | −65°8 (1, CH$_3$OH) | 52.88 | 4.78 | 9.49 | 52.87 | 4.69 | 9.55 |
| 27 | — | I''' | C$_{37}$H$_{41}$F$_6$N$_5$O$_7$ | 781.7 | 202–203 | 60 | −17°6 (1, CH$_3$OH) | 56.84 | 5.28 | 8.96 | 56.90 | 5.25 | 8.87 |

TABLE C

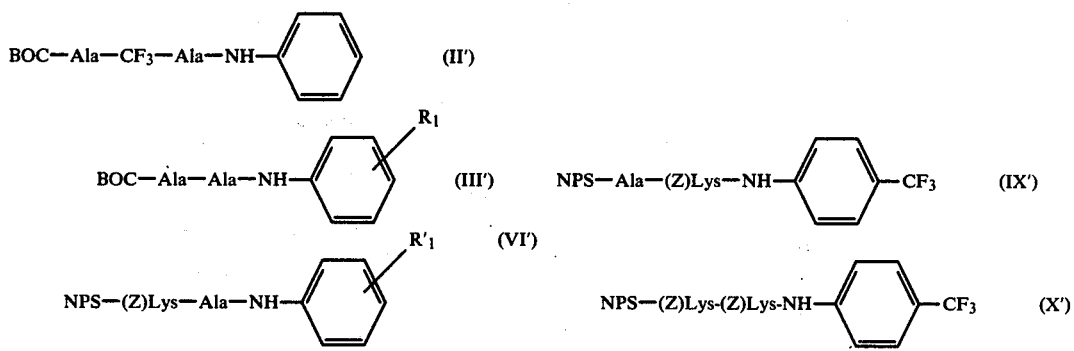

| Code Number | R₁ or R'₁ | Formula | Empirical formula | Molecular Weight | Melting Point (°C.) | Yield (%) | $[\alpha]_{546}^{25}$ | Calculated (%) C | H | N | Obtained (%) C | H | N |
|---|---|---|---|---|---|---|---|---|---|---|---|---|---|
| 28 | 4—CF₃ | VI' | $C_{29}H_{30}SF_3N_4O_5$ | 603.6 | 17—118 | 73 | −94°6 (1, CH₃OH) | 55.63 | 4.98 | 10.81 | 55.73 | 4.89 | 10.50 |
| 29 | H | VI' | $C_{28}H_{31}SN_4O_5$ | 535.6 | 174 | 70 | −91° (1, CH₃OH) | | | | | | |
| 30 | — | X' | $C_{39}H_{41}SF_3N_5O_9$ | 812.8 | 150–153 | 79 | −57°7 (0.5,CH₃OH) | 58.70 | 5.40 | 10.02 | 58.51 | 5.26 | 9.99 |
| 31 | — | II' | $C_{17}H_{22}F_3N_3O_4$ | 389.4 | 185–190 | 75 | | 52.44 | 5.69 | 10.79 | 52.59 | 5.62 | 11.00 |
| 32 | — | IX' | $C_{29}H_{30}F_3SN_4O_5$ | 603.6 | 227–229 | 66 | −53°4 (0.5,CH₃OH) | 55.63 | 4.98 | 10.81 | 55.68 | 4.99 | 10.78 |
| 34 | 3CF₃ | III' | $C_{18}H_{24}F_3N_3O_4$ | 403.4 | 175 | 56 | | | | | | | |

TABLE D

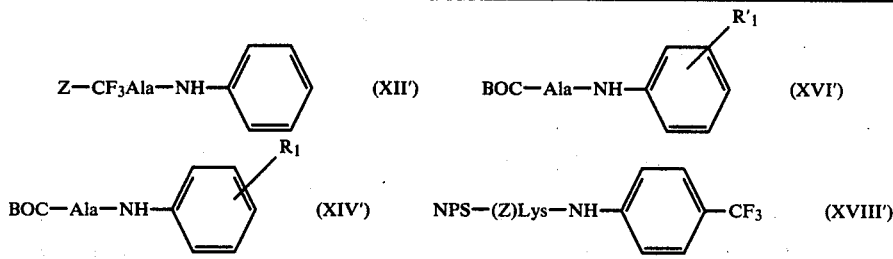

| Code Number | R₁ or R'₁ | Formula | Empirical formula | Molecular Weight | Melting Point (°C.) | Yield (%) | $[\alpha]_{546}^{25}$ | Calculated (%) C | H | N | Obtained (%) C | H | N |
|---|---|---|---|---|---|---|---|---|---|---|---|---|---|
| 35 | 4CF₃ | XVI' | $C_{15}H_{19}F_3N_2O_3$ | 332.3 | 158–159 | 77 | −50° (1, MeOH) | 54.21 | 5.76 | 8.48 | 54.42 | 5.62 | 7.94 |
| 36 | H | XVI' | $C_{14}H_{20}N_2O_3$ | 264.3 | 175 | 72 | −61°2 (1, CH₃OH) | | | | | | |
| 38 | 3CF₃ | XIV' | $C_{15}H_{19}F_3N_2O_3$ | 332.3 | 123 | 75 | | | | | | | |
| 39 | — | XII' | $C_{16}H_{14}F_3N_2O_3$ | 339.2 | 129–130 | 77 | | | | | | | |
| 40 | — | XVIII' | $C_{26}H_{25}SF_3N_4O_5$ | 562.6 | 136–138 | 35 | 0°3 (1, CH₃OH) | 56.24 | 4.72 | 9.72 | 56.20 | 4.75 | 9.38 |

The compounds of formula (I) were tested in vitro and revealed properties as reversible inhibitors of the porcine pancreatic elastase and of the human leucocytal elastase. This latter was purified according to the Travis method (Baugh, R. J. and Travis, J. (1976), Biochemistry, 15, 4, 836). The method of study used is the conventional method of Dixon (Dixon, M., (1953), Biochemical Journal, 55, 1970) for measuring the inhibition constants K$_I$ of the compounds of the invention with regard to the hydrolysis reactions of the succinyl-tri-L-alanine-paranitroanilide catalysed by the two above elastases (Bieth J., Spiess B. and Wermuth C. G. (1974) Biochemical Medicine, 11, 350). In certain cases (leucocytal elastase) the inhibitory power of the compounds studied was measured by means of the I$_{50}$ concentration of these compounds inducing 50% inhibition of the hydrolysis of the succinyl-tri-alanine-paranitroanilide at a 10$^{-3}$ M concentration catalysed by the enzyme. These latter measurements were achieved in the presence of 5% DMF. All the measurements were made at 25° C. in a 0.2 Molar buffer solution of tri-hydroxymethyl-aminomethane at pH 8.

Table E below lists the results obtained for the compounds of formula (I) as well as the reference compounds (A), acetyl-L-prolyl-L-alanyl-L-prolyl-L-alaninal, for the pancreatic elastase (Thompson, R. C., Biochemistry (1973), 17, 1, 47) and (B), oleic acid, for the leucocytal elastase (Ashe, B. M. and Zimmerman, M. (1977), Biochem. Biophys. Res. Comm., 75, 194).

TABLE E (Values of inhibition constants K$_I$ on pancreatic and leucocytal elastases and I$_{50}$ values on the leucocytal elastase of the compounds of formula (I), at 25° C. in TRIS 0.2 M buffer, pH 8.)

| Code member | $K_T^{(a)}$ pancreatic (M) | $K_T^{(a)}$ leucocytal (M) | $T_{50}^{(b)}$ leucocytal (M) |
|---|---|---|---|
| 1 | 2.5 . 10⁻⁷ | | 2.5 . 10⁻⁴ |
| 2 | 1.1 . 10⁻⁷ | | 10⁻⁴ |
| 3 | 1.2 . 10⁻⁷ | | 7.8 . 10⁻⁵ |
| 4 | 3.8 . 10⁻⁷ | | 1.5 . 10⁻⁴ |
| 5 | 9 . 10⁻⁸ | | 5.6 . 10⁻⁵ |
| 6 | 8 . 10⁻⁷ | | 1.2 . 10⁻⁴ |
| 7 | 2.9 . 10⁻⁷ | | 3 . 10⁻⁵ |
| 8 | 5.5 . 10⁻⁷ | | 1.2 . 10⁻⁵ |
| 9 | 1.1 . 10⁻⁷ | | 10⁻⁴ |

TABLE E-continued (Values of inhibition constants
$K_I$ on pancreatic and leucocytal elastases and
$I_{50}$ values on the leucocytal
elastase of the compounds of formula (I), at
25° C. in TRIS 0.2 M buffer, pH 8.)

| Code member | $K_I^{(a)}$ pancreatic (M) | $K_I^{(a)}$ leucocytal (M) | $T_{50}^{(b)}$ leucocytal (M) |
|---|---|---|---|
| 10 | $2 \cdot 10^{-7}$ | | $4.7 \cdot 10^{-4}$ |
| 11 | $4 \cdot 10^{-8}$ | $4.4 \cdot 10^{-5}$ | $1.5 \cdot 10^{-4}$ |
| 12 | $2.5 \cdot 10^{-8}$ | $3 \cdot 10^{-6}$ | $3.5 \cdot 10^{-5}$ |
| 13 | $3 \cdot 10^{-8}$ | $1.4 \cdot 10^{-5}$ | $5 \cdot 10^{-5}$ |
| 14 | $5 \cdot 10^{-8}$ | $7 \cdot 10^{-7}$ | $5.7 \cdot 10^{-6}$ |
| 15 | $7 \cdot 10^{-8}$ | $7 \cdot 10^{-7}$ | $4.8 \cdot 10^{-6}$ |
| 16 | $3.2 \cdot 10^{-8}$ | $2.5 \cdot 10^{-6}$ | $9 \cdot 10^{-6}$ |
| 17 | $2.7 \cdot 10^{-7}$ | | $4 \cdot 10^{-4}$ |
| 18 | $1.5 \cdot 10^{-7}$ | | $1.4 \cdot 10^{-4}$ |
| 19 | $4 \cdot 10^{-7}$ | | $1.5 \cdot 10^{-4}$ |
| A | $8 \cdot 10^{-7}$ | | |
| B | | $9 \cdot 10^{-6}$ | |

$^{(a)}$The values were obtained in the absence of any organic solvent
$^{(b)}$The values were obtained in the presence of 50 % dimethylformamide Furthermore, the toxicity of the compounds of the invention were studied intravenously on mice. More exactly, these compounds were tested in the form of a solution in physiological serum containing 10% DMF.

Thus, by way of example, no case of mortality was observed consequent on the administration of 20, 40 and 80 mg/kg respectively of the compound of code number 3. It is to be noted that it was not possible to use doses higher than those indicated above, because of the solubility limit of compound 3.

Because of their interesting pharmacological property, the compounds of the invention find then their application in the therapeutical field and they are particularly indicated in the treatment of emphysema. They are administered in the form of aerosols (0.5 to 100 mg of active ingredient), parenterally (2 to 6 ampoules per day containing from 0.5 to 50 mg of active ingredient), orally (pills or gelules: 2 to 6 per day containing from 2 to 400 mg of active ingredient) or rectally (1 to 2 suppositories per day containing from 2 to 400 mg of active ingredient).

We claim:

1. Compounds of formula:

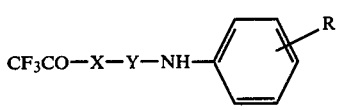

(I)

in which the couple —X—Y— represents:
either the sequence -L-Ala-L-Ala, in which case R designates:
a hydrogen atom;
a nitro or trifluoromethyl group in the meta position; or
a chlorine atom or a nitro, trifluoromethyl, methoxy, isopropyl, cyano or carboxyl group in the para position;
or the sequence -L-Lys-L-Ala-, in which case R designates:
a hydrogen atom; or
a trifluoromethyl, methyl, isopropyl, N,N-dimethylamino or acetyl group in the para position;
or the sequence —L—Ala—DL—Ala—,
|
CF$_3$ in which case R designates a hydrogen atom;
or the sequence -L-Lys-L-Lys or -L-Ala-L-Lys-, in which case R represents a trifluoromethyl group in the para position.

2. A compound having the formula

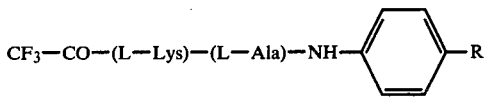

wherein R is H, p-CF$_3$, p-CH$_3$, p-CH(CH$_3$)$_2$, p-N(CH$_3$)$_2$ or p-COCH$_3$.

3. A compound according to claim 2 having the formula

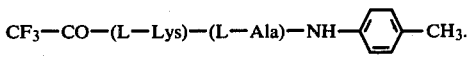

4. A compound according to claim 2 having the formula

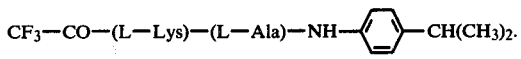

5. A compound according to claim 2 having the formula

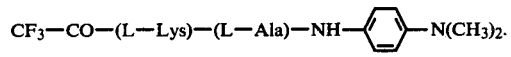

6. A compound according to claim 2 having the formula

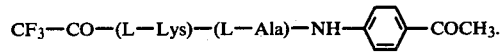

7. A compound according to claim 2 having the formula

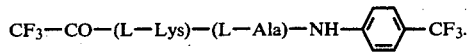

8. A compound having the formula

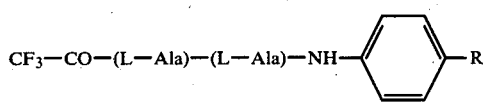

wherein R is H, m-NO$_2$, m-CF$_3$, p-Cl, p-NO$_2$, p-CF$_3$, p-OCH$_3$, p-CH(CH$_3$)$_2$, p-CN or p-COOH.

9. A compound having the formula

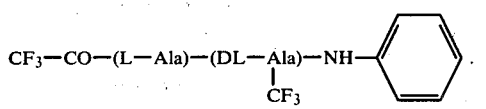

10. A compound having the formula

11. A compound having the formula
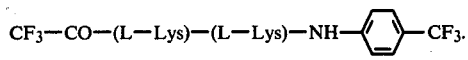
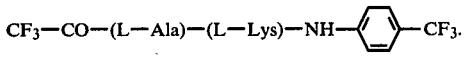
12. A pharmaceutical composition comprising a compound as claimed in claim 1 with an effective amount of a pharmaceutically acceptable carrier.
* * * * *